United States Patent [19]

Loughner et al.

[11] Patent Number: 5,677,333

[45] Date of Patent: Oct. 14, 1997

[54] METHOD FOR CONTROLLING PHYTOPATHOGENIC FUNGI

[75] Inventors: Daniel Louis Loughner, Huntingdon Valley; Enrique Luis Michelotti, Fort Washington; Willie Joe Wilson, Chalfont; David Hamilton Young, Ambler, all of Pa.

[73] Assignee: Rohm and Haas Company, Philadelphia, Pa.

[21] Appl. No.: 676,845

[22] Filed: Jul. 8, 1996

[51] Int. Cl.$^6$ ............... A01N 37/18; A01N 37/34; A01N 47/10; A01N 47/40

[52] U.S. Cl. ............... 514/491; 514/476; 514/514; 514/515; 514/516; 514/522; 514/617; 514/622

[58] Field of Search ............... 514/514, 515, 514/516, 476, 491, 522, 617, 622

[56] References Cited

U.S. PATENT DOCUMENTS 5,304,572  4/1994  Michelotti et al. ............... 514/514

*Primary Examiner*—Allen J. Robinson
*Attorney, Agent, or Firm*—Joseph F. Leightner

[57] ABSTRACT

A method for controlling phytopathogenic fungi comprises applying a selected fungicidally active N-acetonylbenzamide compound and a second fungicidally active compound selected from the group consisting of manganese-zinc ethylenebis(dithiocarbamate), manganese ethylenebis(dithiocarbamate), zinc ammoniate ethylenebis (dithiocarbamate), zinc ethylenebis(dithiocarbamate), 2-cyano-N-((ethylamino)carbonyl)-2-(methoxyimino) acetamide, and (E,Z) 4-(3-(4-chlorophenyl)-3-(3,4-dimethoxyphenyl)acryloyl)morpholine to plant seed, to plant foliage or to a plant growth medium and provides higher fungicidal activity than separate use of the same compounds.

10 Claims, No Drawings

METHOD FOR CONTROLLING PHYTOPATHOGENIC FUNGI

The present invention regards a method for controlling phytopathogenic fungi plants.

U.S. Pat. No. 5,304,572 discloses applying mixtures of the N-acetonylbenzamides disclosed therein with other fungicidal compounds. It has now been discovered that application of the N-acetonylbenzamides disclosed in the '572 patent in combination with selected other fungicidal compounds provides unexpectedly high fungicidal activity and is effective in controlling phytopathogenic fungi at lower N-acetonylbenzamide dosage rates than those disclosed in the '572 patent.

A method for controlling phytopathogenic fungi on a plant comprises:

applying:

a fungicidally effective amount of a first fungicidally active compound having the structural formula (1):

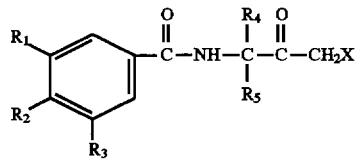

or an agronomically acceptable salt thereof, wherein:

$R_1$ and $R_3$ are each independently halo, or $(C_1-C_4)$alkyl;

$R_2$ is $(C_1-C_4)$alkyl, $(C_2-C_4)$alkenyl, $(C_2-C_6)$alkynyl, $(C_1-C_4)$alkoxy, or cyano;

$R_4$ and $R_5$ are independently H, or $(C_1-C_4)$alkyl, provided that at least one of $R_4, R_5$ is $(C_2-C_4)$alkyl; and X is halo, thiocyano, or isothiocyano; and a fungicidally effective amount of a second fungicidally active compound selected from the group consisting of:
manganese-zinc ethylenebis(dithiocarbamate);
manganese ethylenebis(dithiocarbamate);
zinc ammoniate ethylenebis(dithiocarbamate);
zinc ethylenebis(dithiocarbamate);
2-cyano-N-((ethylamino)carbonyl)-2-(methoxyimino) acetamide; and
(E,Z) 4-(3-(4-chlorophenyl)-3-(3,4-dimethoxyphenyl) acryloyl)morpholine to the plant seed, to the plant foliage or to the growth medium for the plant.

"$(C_1-C_4)$alkyl" means a straight or branched alkyl group having one to four carbon atoms per group and includes methyl, ethyl, n-propyl, iso-propyl, n-butyl, iso-butyl, sec-butyl and tert-butyl.

"$(C_2-C_4)$alkenyl" means a straight or branched alkenyl group having two to four carbon atoms per group and includes, e.g., ethenyl, 2-propenyl, 2-butenyl, 1-methylethenyl, 2-methyl-2-propenyl.

"$(C_2-C_6)$alkynyl" means a straight or branched alkynyl group having from two to six carbons per group and includes, e.g., ethynyl, 2-propynyl, 2-butynyl.

"Halo" means chloro, fluoro, bromo and iodo.

"$(C_1-C_4)$alkoxy" means a straight or branched alkoxy group having one to four carbon atoms per group and includes, e.g., methoxy, ethoxy, propoxy, isopropoxy, butoxy, isobutoxy, sec-butoxy and tert-butoxy.

"Cyano" means a group having the structural formula —CN.

"Thiocyano" means a group having the structural formula —SCN.

"Isothiocyano" means a group having the structural formula —NCS.

Agronomically acceptable salts include, e.g., metal salts such as sodium, potassium, calcium and magnesium salts, ammonium salts such as isopropyl ammonium salts and trialkylsulfonium salts such as triethylsulfonium salts.

The first fungicidally active compound may be a single compound having the structural formula (1) or, alternatively, may be a mixture of compounds each having the structural formula (1). Suitable compounds according to structural formula (1) include, for example:

N-[3'(1'-chloro-3'-methyl-2'-oxopentan]-3,5-dichloro-4-methylbenzamide;

N-[3'-(1'-chloro-3'-methyl-2'-oxopentan]-3,5-dichloro-4-ethylbenzamide;

N-[3'-(1'-chloro-3'-methyl-2'-oxopentan]-3,5-dichloro-4-ethoxybenzamide;

N-[3'-(1'-chloro-3'-methyl-2'-oxopentan]-3,5-dichloro-4-methoxybenzamide;

N-[3'-(1'-chloro-3'-methyl-2'-oxopentan]-3,5-dichloro-4-cyanobenzamide; or

N-[3'-(1'-chloro-3'-methyl-2'-oxopentan]-3,5-dibromo-4-methylbenzamide.

In a highly preferred embodiment, the first fungicidally active compound is N-[3'-(1'-chloro-3-methyl-2'-oxopentan]-3,5-dichloro-4-methylbenzamide, N-[3'-(1'-chloro-3'-methyl-2'-oxopentan]-3,5-dibromo-4-cyanobenzamide or a mixture thereof. More preferably, the N-acetonyl benzamide compound according to formula (1) is N-[3'(1'-chloro-3'-methyl-2'-oxopentan]-3,5-dichloro-4-methylbenzamide.

The method of the present invention may optionally further comprise application of other compounds having biological activity, e.g., additional fungicidally active compounds or compounds having herbicidal activity or insecticidal activity, to the plant seed, to the plant foliage or to the growth medium for the plant.

The method of the present invention is useful for the control of phytopathogenic fungi on crops and the first and second fungicidally active compounds may be applied as a soil fungicide, as a seed protectant, as a foliar fungicide or as a combination thereof. In a preferred embodiment, the first and second fungicidally active compounds are applied to a plant growth medium, to the plant seed or to plant foliage at dosage rates of from 2 parts by weight (pbw) to 90 pbw, more preferably from 5 pbw to 75 pbw, of the first fungicidally active compound per 100 pbw of the combined amount of first and second fungicidally active compounds and from 10 pbw to 98 pbw, more preferably from 25 pbw to 95 pbw, of the second fungicidally active compound per 100 pbw of the combined amount of first and second fungicidally active compounds.

As a soil fungicide, the first and second fungicidally active compositions can be incorporated in the soil or applied to the surface of the soil at a dosage rate of about 0.25 kg to 5 kg of the first fungicidally active compound and from 0.25 kg to 5 kg of the second fungicidally active compound per hectare.

As a seed protectant, the first and second fungicidally active compounds are coated on seed at a dosage rate of about 0.5 kilograms (kg) to 5 kg of the first fungicidally active compound and from 0.5 kg to 5 kg of the second fungicidally active compound per 100 kg seed.

As a foliar fungicide, the first and second fungicidally active compounds are applied to plant foliage at a dosage rate of from 0.01 kg per hectare to 5 kg per hectare of the first fungicidally active compound, and a dosage rate of from 0.05 kg per hectare to less than 5 kg per hectare of the second fungicidally active compound. In a preferred embodiment, the first fungicidally active compound is applied to plant foliage at a dosage rate of from 0.05 kg per hectare to less than 0.1 kg per hectare. In a preferred embodiment, the second fungicidally active compound is applied to plant foliage at a dosage rate of 0.1 kg per hectare to 2.0 kg per hectare. The first and second fungicidally active compounds can be applied to plant foliage as fungicidal spays by methods commonly employed, such as conventional high-gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.1 kg to about 5 kg, preferably 0.2 kg to 2.5 kg, of both the first and second active compounds per hectare.

The first and second fungicidally active compounds may be applied simultaneously or sequentially.

In a preferred embodiment, the first and second fungicidally active compounds are simultaneously applied to plant growth medium, the plant seed, plant foliage or a combination thereof as a composition comprising a mixture of the first fungicidally active compound and second fungicidally active compound.

In a first highly preferred embodiment the mixture includes from 2 pbw to 50 pbw, more preferably from 5 pbw to 25 pbw, of a first fungicidally active compound and from 50 pbw to 98 pbw, more preferably from 75 pbw to 95 pbw, of a second fungicidally active compound selected from the group consisting of (manganese-zinc ethylenebis (dithiocarbamate), manganese ethylenebis (dithiocarbamate), zinc ammoniate ethylenebis (dithiocarbamate), zinc ethylenebis(dithiocarbamate) and mixtures thereof, per 100 pbw of the mixture.

In a second highly preferred embodiment the mixture includes from 10 pbw to 90 pbw, more preferably from 20 pbw to 80 pbw, of a first fungicidally active compound and from 10 pbw to 90 pbw, more preferably from 20 pbw to 80 pbw, of 2-cyano-N-((ethylamino)carbonyl)-2-(methoxyimino)acetamide per 100 pbw of the mixture.

In a third highly preferred embodiment the mixture includes from 10 pbw to 90 pbw, more preferably from 20 pbw to 80 pbw, of a first fungicidally active compound and from 10 pbw to 90 pbw, more preferably from 20 pbw to 80 pbw, of (E,Z) 4-(3-(4-chlorophenyl)-3-(3,4-dimethoxyphenyl)acryloyl) morpholine per 100 pbw of the mixture.

In an alternative embodiment, the first and second fungicidally active compounds are applied sequentially to the plant seed, plant foliage or plant growth medium, with application of the second-applied compound following application of the first-applied compound by up to 72 hours. The compounds may be applied in either order, i.e., the first fungicidally active compound followed by the second fungicidally active compound or, alternatively, as application of the second fungicidally active compound followed by the first fungicidally active compound.

The method of the present invention is useful in controlling certain phytopathogenic fungi, particularly fungi of the class Oomycetes, and provides high fungicidal activity and relatively low phytotoxicity. The method of the present invention is particularly effective in controlling Oomycete fungi of the genera Phytophthora, Plasmopara, Peronospora, Albugo and, Pseudoperonospora, and even more particularly against the organisms of those genera that cause diseases such as late blight in tomatoes and potatoes and downy mildew in grapes and other crops, including, for example, *Phytophthora infestans, Plasmopara viticola, Pseudoperonospora cubensis.*

For each of the above disclosed purposes, the first and second fungicidally active compounds can be used in the technical or pure form as prepared, as solutions or as formulations. The compounds are usually taken up in a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated. It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's Emulsifiers and Detergents, McCutcheon's Emulsifiers and Detergents/Functional Materials and McCutcheon's Functional Materials all published annually by McCutcheon Division of MC Publishing Company (New Jersey).

In general, the compositions utilized in this invention can be dissolved in appropriate solvents such as acetone, methanol, ethanol, dimethylformamide or dimethyl sulfoxide and such solutions extended with water. The concentrations of the combined first and second active compounds in the solution can vary from 1% to 90% with a preferred range being 5% to 50%.

For the preparation of emulsifiable concentrates, the compositions used in the invention can be dissolved in suitable organic solvents or a mixture of solvents, together with an emulsifying agent which permits dispersion of the first and second active compounds in Water. The concentration of the combined first and second active compounds in emulsifiable concentrates is usually 10% to 90% and in flowable emulsion concentrates, this can be as high as 75%. Wettable powders suitable for spraying, can be prepared by admixing the composition with a finely divided solid, such as clays, inorganic silicates and carbonates, and silicas and incorporating wetting agents, sticking agents, and/or dispersing agents in such mixtures. The concentration of the combined first and second active compounds in such formulations is usually in the range of 20% to 98%, preferably 40% to 75%.

Dusts are prepared by mixing the composition of the present invention, or salts and complexes thereof, with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the combined first and second active compounds are commonly made and are subsequently diluted to 1% to 10% use concentration.

The benefit provided by the present method, i.e., the improved fungicidal activity of the combined application of the first and second fungicidal compounds relative to the fungicidal activity exhibited by each of the two compounds when used separately, becomes more pronounced as the length of the interval between fungicide applications increases. Use of the present method is thus particularly advantageous should the intended application schedule be interrupted, e.g., due to inclement weather.

The results provided by the mixtures were compared with the predicted results that were calculated using the formula set forth by S. R. Colby in Weeds 1967, 15, 20–22 ("Colby's Formula") from the results obtained using each of the compounds individually. The predicted results are also provided in the following Examples.

EXAMPLE 1

A field test of the method of the present invention was conducted in South Auckland, New Zealand. Test plots consisted of four rows, each 15 meters long, of potato plants, cultivar Ilam Hardy. Four such plots arranged in randomized blocks were used for each treatment.

Fungicide treatments were applied at 7-day or 14-day intervals over a 10-week period. N-[3'(1'-chloro-3'-methyl-2'-oxopentan]-3,5-dichloro-4-methylbenzamide was applied as a flowable formulation (23% active ingredient). Manganese-zinc ethylenebis (dithiocarbamate) was applied as a wettable powder formulation (DITHANE™ M-45, 80WP, Rohm and Haas Company). The two compounds were each applied individually in the manner disclosed above and in combination as an aqueous tank mix of the two compounds.

Assessments of disease in response to natural infection were made of plants in the two center rows at evaluation intervals of 5, 6, 7, 8, 9, 10,and 11 weeks after the first treatment.

The compounds applied (Compound), the dosage rates of the compounds applied, expressed in grams of active ingredient per hectare (Dosage Rate, (g/ha)), the application interval, expressed in days (Application Interval (days)) and results, expressed as percent disease control for each evaluation interval (% Control by Evaluation Interval) are set forth below in TABLE 1 for treatment with N-[3'(1'-chloro-3'-methyl-2'-oxopentan]-3,5-dichloro-4-methylbenzamide, treatment with manganese-zinc ethylenebis (dithiocarbamate) and treatment with a mixture of the two compounds. The results provided by the mixture were compared with predicted results that were calculated using the Colby Formula.

TABLE 1

*Phytophthora infestans*, Potatoes; New Zealand

| Compound | Dosage Rate (g/ha) | Application Interval (days) | % Control by Evaluation Interval[a] | | | | | | |
|---|---|---|---|---|---|---|---|---|---|
| | | | 5 weeks | 6 week | 7 weeks | 8 weeks | 9 weeks | 10 weeks | 11 weeks |
| untreated | — | — | 0 | 0 | 0 | 0 | 0 | 0 | 0 |
| A | 150 | 7 | 199 | 97 | 88 | 44 | 116 | 11 | 1 |
| M | 1600 | 7 | 99 | 98 | 95 | 87 | 79 | 66 | 29 |
| A/M | 150/1600 | 7 | 100 (100) | 100 (100) | 99 (99) | 96 (93) | 94 (82) | 84 (70) | 31 (30) |
| A | 150 | 14 | 98 | 81 | 56 | 17 | 11 | 6 | 0 |
| M | 1600 | 14 | 98 | 88 | 80 | 62 | 38 | 16 | 6 |
| A/M | 150/1600 | 14 | 100 (100) | 99 1 (98) | 98 1 (91) | 92 1(68) | 87 1(45) | 61 1(21) | 14 1(6) |

A = N-[3'(1'-chloro-3'-methyl-2'-oxopentan]-3,5-dichloro-4-methylbenzamide
M = manganese-zinc ethylenebis(dithiocarbamate)
[a]Predicted % Control values are set forth in parentheses following the observed Control values

EXAMPLE 2

A field test of the method of the present invention was conducted in the State of Maine, U.S.A. Plots consisted of three rows, each 26.3 feet long, of potato plants, cultivar Katahdin. Five such plots arranged in randomized blocks were used for each treatment.

Fungicide treatments were applied at day 0,and at 14, 23, 33 and 43 days thereafter. N-[3'(1'-chloro-3'-methyl-2'-oxopentan]-3,5-dichloro-4-methylbenzamide was applied as a flowable formulation (23% active ingredient), and manganese-zinc ethylenebis(dithiocarbamate) as a wettable powder formulation (DITHANE™M-45, 80WP, Rohm and Haas Company). The two compounds were each applied individually in the manner disclosed above and in combination as an aqueous tank mix of the two compounds. Plots were inoculated with spores of *Phytophthora infestans* at 2 and 8 days following the first fungicide application.

Disease evaluations were made on the center row of each plot 49 days after the first fungicide application, at which time the untreated control plants were completely defoliated.

The compounds applied (Compound), dosage rates of the compounds applied, expressed as grams of active ingredient per hectare (Dosage Rate, (g/ha)) and results, expressed as percent disease control based on measurement of the percent defoliation of the treated plants (% Control (Observed)), are set forth below in TABLE 2 for treatment with N-[3'(1'-chloro-3'-methyl-2'-oxopentan]-3,5-dichloro-4-methylbenzamide, treatment with manganese-zinc ethylenebis(dithiocarbamate) and treatment with a mixture of the two compounds. The result provided by the mixture was compared with a predicted result that was calculated using Colby's formula from the results obtained using each of the compounds individually.

TABLE 2

Phytophthora infestans, Potatoes, Maine, U.S.A.

| Compound | Dosage Rate (g/ha) | % Control (Observed) | % Control (Predicted by Colby Equation) |
| --- | --- | --- | --- |
| untreated | — | 0 | — |
| A | 300 | 23 | — |
| M | 1000 | 69 | — |
| A/M | 300/1000 | 92 | 76 |

A = N-[3'(1'-chloro-3'-methyl-2'-oxopentan]-3,5-dichloro-4-methylbenzamide
M = manganese-zinc ethylenebis(dithiocarbamate)

EXAMPLE 3

A field test of the method of the present invention was conducted in Pavia, Italy on grape vines.

N-[3'(1'-chloro-3-methyl-2'-oxopentan]-3,5-dichloro-4-methylbenzamide was applied as a flowable formulation (23% active ingredient), and manganese-zinc ethylenebis (dithiocarbamate) as a wettable powder formulation (DITHANE™ M-45, 80WP). The two compounds were each applied individually in the manner disclosed above and in combination as an aqueous tank mix of the two compounds. Fungicide treatments were applied at 14-day intervals. The plots were inoculated with a spore suspension of *Plasmopara viticola* 3 days after the first fungicide application.

Evaluations of disease on the foliage were made 4 weeks after the first application of fungicide. The compounds applied (Compound), the dosage rates of the compounds applied, expressed in grams of active ingredient per hectare (Dosage Rate, (g/ha)) and results, expressed as percent disease control in comparison with untreated plots (% Control (Observed)), are set forth below in TABLE 3 for treatment with N-[3'(1'-chloro-3'-methyl-2'-oxopentan]-3,5-dichloro-4-methylbenzamide, treatment with manganese-zinc ethylenebis(dithiocarbamate) and treatment with a mixture of the two compounds. The result provided by the mixture was compared with a predicted result that was calculated using Colby's Formula from the results obtained using each of the compounds individually.

TABLE 3

Plasmopara viticola, Grapes, Italy

Phytophthora infestans, Potatoes, Maine, U.S.A.

| Compound | Dosage Rate (g/ha) | % Control (Observed) | % Control (Predicted by Colby Equation) |
| --- | --- | --- | --- |
| untreated | — | 0 | — |
| A | 300 | 87 | — |
| M | 1600 | 61 | — |
| A/M | 300/1600 | 97 | 95 |

A = N-[3'(1'-chloro-3'-methyl-2'-oxopentan]-3,5-dichloro-4-methylbenzamide
M = manganese-zinc ethylenebis(dithiocarbamate)

EXAMPLE 4

The trial was conducted in the State of Michigan, U.S.A. Plots consisted of 4 grape vines, cultivar Chancellor. Four such plots arranged in randomized blocks were used for each treatment.

Fungicide treatments were applied at day 0, and at 13, 28, 43, 55, 71, and 84 days thereafter. N-[3'(1'-chloro-3'-methyl-2'-oxopentan]-3,5-dichloro-4-methylbenzamide was applied as a flowable formulation (23% active ingredient) at 100 grams of active ingredient per hectare, and 2-cyano-N-(ethylamino)carbonyl)-2-(methoxyimino)acetamide was applied as a wettable powder formulation (CURZATE™, 50WP, DuPont, Wilmington, Del.) at 100 grams of active ingredient per hectare. The two compounds were also applied as an aqueous tank mix of the two compounds at a dosage of 100 grams of active ingredient per hectare of each compound.

Evaluation of disease in response to natural infection was made 12 days after the last treatment. The incidence and severity of downy mildew fruit rot was determined for twenty clusters of fruit selected randomly from the middle two vines of each plot. Incidence refers to whether or not the cluster was diseased, and severity is the percentage of diseased fruit surface area. The compounds applied (Compound), and the incidence and severity results, expressed as percent disease control in comparison with untreated plots (% Control, Incidence (Observed) and % Control, Severity (Observed), respectively) are set forth below in TABLE 4 for treatment with N-[3'(1'-chloro-3'-methyl-2'-oxopentan]-3,5-dichloro-4-methylbenzamide, treatment with 2-cyano-N-((ethylamino)carbonyl)-2-(methoxyimino)acetamide and treatment with a mixture of the two compounds. The results obtained using the mixture of the two compounds were compared with predicted results that were calculated using Colby's formula from the results obtained using each of the compounds individually. The predicted results for incidence and severity are set forth below in TABLE 4 as "% Control, Incidence (Predicted)" and "% Control, Severity (Predicted)", respectively.

TABLE 4

Plasmopara viticola, Grapes, Michigan, U.S.A.

| Compound | % Control, Incidence (Observed) | % Control, Incidence (Predicted) | % Control, Severity (Observed) | % Control, Severity (Predicted by Colby Equation) |
|---|---|---|---|---|
| untreated | 0 | — | 0 | — |
| A | 43.7 | — | 75.3 | — |
| C | 2.5 | — | 34.6 | — |
| A/C | 100 | 45.1 | 100 | 83.8 |

A = N-[3'(1'-chloro-3'-methyl-2'-oxopentan]-3,5-dichloro-4-methylbenzamide
C = 2-cyano-N-((ethylamino)carbonyl)-2-(methoxyimino)acetamide

EXAMPLE 5

N-[3'(1'-chloro-3'-methyl-2'-oxopentan]-3,5-dichloro-4-methylbenzamide and dimethomorph ((E,Z) 4-(3-(4-chlorophenyl)-3-(3,4-dimethoxyphenyl)acryloyl) morpholine) (technical materials) were dissolved in acetone/methanol/water (1:1:2), and the solutions combined to give mixtures of the desired compositions. Each of the solutions and the mixtures were then applied to the foliage of tomato plants at the treatment rates set forth below in TABLE 5.

Cultures of *Phytophthora infestans* were maintained on V8 juice agar. Spore suspensions prepared from 1–2 week old plates were used to inoculate tomato seedlings which were about 2 weeks old. A DeVilbiss atomizer was used to apply the spores to the fungicide-treated foliage. The plants were kept in a humidity cabinet for 24 hours after inoculation and then placed in a controlled temperature chamber for disease development.

Disease evaluations were made 6 days after inoculation. The compounds applied and dosage rates, expressed in parts per million (Dosage Rate (ppm)/Compound) and results, expressed as percent disease control in comparison to untreated plants (% Control (Observed)), are set forth below in TABLE 5 for treatment with N-[3'(1'-chloro-3'-methyl-2'-oxopentan]-3,5-dichloro-4-methylbenzamide, treatment with ((E,Z) 4-(3-(4-chlorophenyl)-3-(3,4-dimethoxyphenyl) acryloyl)morpholine) and treatment with mixtures of the two compounds. The results provided by the mixtures were compared with predicted results that were calculated using Colby's formula from the results obtained using each of the compounds individually.

TABLE 5

Phytophthora infestans, Tomatoes, Greenhouse

| Dosage Rate (ppm)/Compound | % Control (Observed) | % Control (Predicted by Colby Equation) |
|---|---|---|
| untreated | 0 | — |
| 0.4 ppm A | 0 | — |
| 0.8 ppm A | 20 | — |
| 0.4 ppm D | 0 | — |
| 0.8 ppm D | 10 | — |
| 1.5 ppm D | 35 | — |
| 0.4 ppm A, 0.4 ppm D | 30 | 0 |
| 0.4 ppm A, 0.8 ppm D | 30 | 10 |
| 0.4 ppm A, 1.5 ppm D | 48 | 35 |
| 0.8 ppm A, 0.4 ppm D | 70 | 20 |
| 0.8 ppm A, 0.8 ppm D | 66 | 28 |
| 0.8 ppm A, 1.5 ppm D | 65 | 48 |

A = N-[3'(1'-chloro-3'-methyl-2'-oxopentan]-3,5-dichloro-4-methylbenzamide
D = (E,Z)4-(3-(4-chlorophenyl)-3-(3,4-dimethoxyphenyl)acryloyl) morpholine

EXAMPLE 6

A field trial was conducted in Campinas, Brazil. Plots each consisted of 4 grape vines, cultivar Maria.

Fungicide treatments were applied at 7-day intervals with a total of 5 applications. N-[3'(1'-chloro-3'-methyl-2'-oxopentan]-3,5-dichloro-4-methylbenzamide was applied as a flowable formulation (23% active ingredient), 2-cyano-N-((ethylamino)carbonyl)-2-(methoxyimino)acetamide as a wettable powder formulation (CURZATE™, 50WP, DuPont, Wilmington, Del). The two compounds were each applied individually in the manner disclosed above and in combination as an aqueous tank mix of the two compounds.

Evaluation of disease in response to a heavy natural infection was made 6 days after the third application, and 7 days after the fifth application. The Compounds applied and dosage rates, expressed as grams of active ingredient per hectare (Compound Dosage Rate (g/ha)) and the results, expressed as percent disease control in comparison with untreated plots (% Control(Observed)) are set forth below in TABLE 6 for treatment with N-[3'(1'-chloro-3'-methyl-2'-oxopentan]-3,5-dichloro-4-methylbenzamide, treatment with 2-cyano-N-((ethylamino)carbonyl)-2-(methoxyimino) acetamide and treatment with mixtures of the two compounds. The results obtained using the mixtures of the two compounds were compared with those predicted by Colby's formula from the results provided by each of the two compounds used individually. The predicted results are set forth below in TABLE 6 as "% Control (Predicted)".

TABLE 6

Plasmopara viticola, Grapes, Brazil

| Compound A Dosage Rate (g/ha) | Compound C Dosage Rate (g/ha) | % Control (Observed)[a] | % Control (Predicted) | % Control (Observed)[b] | % Control (Predicted) |
|---|---|---|---|---|---|
| 0 | 25 | 71.3 | — | 66.7 | — |
| 0 | 50 | 64.8 | — | 59.6 | — |

TABLE 6-continued

*Plasmopara viticola*, Grapes, Brazil

| Compound A Dosage Rate (g/ha) | Compound C Dosage Rate (g/ha) | % Control (Observed)[a] | % Control (Predicted) | % Control (Observed)[b] | % Control (Predicted) |
|---|---|---|---|---|---|
| 0 | 100 | 74.1 | — | 64.3 | — |
| 100 | 0 | 24.3 | — | 21.4 | — |
| 100 | 25 | 84.9 | 78.3 | 85.7 | 73.8 |
| 100 | 50 | 68.7 | 73.4 | 61.9 | 68.2 |
| 100 | 100 | 91.9 | 80.4 | 87.6 | 71.9 |
| 200 | 0 | 21.8 | — | 26.1 | — |
| 200 | 25 | 82.7 | 77.6 | 81.0 | 75.4 |
| 200 | 50 | 84.9 | 72.5 | 79.6 | 70.1 |
| 200 | 100 | 91.9 | 79.7 | 91.4 | 73.6 |

A = N-[3'(1'-chloro-3'-methyl-2'-oxopentan]-3,5-dichloro-4-metliylbenzamide
C = 2-cyano-N-((ethylamino)carbonyl)-2-(methoxyimino)acetamide
[a]six days after the third treatment
[b]Seven days after the fifth treatment The method of the present invention, wherein an N-acetonylbenzamide and a selected second fungicidally active compound are applied to plant seed, plant foliage or to a plant growth medium, unexpectedly provides higher fungicidal activity than the same compounds used separately. The benefit provided by the present method becomes more pronounced as the length of the interval between fungicide applications increases and use of the present method is thus particularly advantageous should the intended application schedule be interrupted, e.g., due to inclement weather.

We claim:

1. A fungicidal composition comprising synergistic fungicidally effective amounts of a manganese-zinc ethylenebis (dithiocarbamate) complex is provide in a range of from 50 to 98 parts by weight and N-[3'(1'-chloro-3-methyl-2'-oxopentan]-3,5-dichlor-4-methylbenzamide is provided from 2 to 50 parts by weight, based on total weight of active ingredient.

2. The composition of claim 1 wherein manganese-zinc ethylenebis(dithiocarbamate) complex is provide in a range of from 75 to 95 parts by weight and N-[3'(1'-chloro-3-methyl-2'-oxopentan]-3,5-dichlor-4-methylbenzamide is provided from 5 to 25 parts by weight, based on total weight of active ingredient.

3. The composition of clam 1 further comprising a carrier.

4. The composition of claim 12 further comprising a surface-active agent.

5. A method of controlling phytopathogenic fungi on a plant comprising applying to the locus of the plant synergistic fungicidally effective amounts of a manganese-zinc ethylenebis(dithiocarbamate) complex in a range of from 50 to 98 parts by weight: and N-[3'(1'-chloro-3-methyl-2'-oxopetan]-3,5-dichlor-4-methylbenzamide is from 2 to 50 parts by weight, based on total weight of active ingredient.

6. The method of claim 5 wherein the pyhtopathogenic fungi belongs to the class Oomycetes.

7. The method of claim 6 wherein the Oomycetes class are of the genera Phytophthora, Plasmopara, Peronospora, Albugo and Pseudoperonospara.

8. The method of claim 7 wherein the genera are Phytophthora and Plasmopara.

9. The method of claim 5 wherein the plant is a potato plant, tomato plant or a grape plant.

10. The method of claim 5 wherein the a manganese-zinc ethylenebis(dithiocarbamate) complex in a range of from 75 to 95 parts by weight: and N-[3'(1'-chloro-3-methyl-2'-oxopentan]-3,5-dichlor-4-methylbenzamide is from 5 to 25 parts by weight, based on total weight of active ingredient.

* * * * *

UNITED STATES PATENT AND TRADEMARK OFFICE
CERTIFICATE OF CORRECTION

PATENT NO. : 5,677,333
DATED : October 14, 1997
INVENTOR(S) : Daniel Louis Loughner et al.

Page 1 of 2

It is certified that error appears in the above-identified patent and that said Letters Patent is hereby corrected as shown below:

Col. 2, lines 12-13: change
"N-[3'(1'-chloro-3'-methyl-2'-oxopentan]-3,5-dichloro-4-methylbenzamide" to
-- N-[3'-(1'-chloro-3'-methyl-2'-oxopentan]-3,5-dichloro-4-methylbenzamide--

Col. 2, lines 28-29: change
"N-[3'(1'-chloro-3'-methyl-2'-oxopentan]-3,5-dichloro-4-methylbenzamide" to
-- N-[3'-(1'-chloro-3'-methyl-2'-oxopentan]-3,5-dichloro-4-methylbenzamide--

Col. 8, Table 3, line 6: The second title "Phytophthora infestans, Potatoes, Maine, U.S.A." should be deleted.

Col. 11, claim 1, line 35: change "provide" to --provided--
Col. 11, claim 1, lines 35-36: change
"N-[3'(1'-chloro-3-methyl-2'-oxopentan]-3,5-dichlor-4-methylbenzamide" to
--N-[3'-(1'-chloro-3'-methyl-2'-oxopentan]-3,5-dichloro-4-methylbenzamide--

Col. 11, claim 2, lines 42-43: change
"N-[3'(1'-chloro-3-methyl-2'-oxopentan]-3,5-dichlor-4-methylbenzamide" to
--N-[3'-(1'-chloro-3'-methyl-2'-oxopentan]-3,5-dichloro-4-methylbenzamide--

Col. 12, claim 4, line 21: change "claim 12" to --claim 1--

Col. 12, claim 5, lines 28-29: change
"N-[3'(1'-chloro-3-methyl-2'-oxopetan]-3,5-dichlor-4-methylbenzamide" to
--N-[3'-(1'-chloro-3'-methyl-2'-oxopentan]-3,5-dichloro-4-methylbenzamide--

UNITED STATES PATENT AND TRADEMARK OFFICE
CERTIFICATE OF CORRECTION

PATENT NO. : 5,677,333
DATED : October 14, 1997
INVENTOR(S) : Daniel Louis Loughner et al.

It is certified that error appears in the above-identified patent and that said Letters Patent is hereby corrected as shown below:

```
Col. 12, claim 10, lines 42-43: change
"N-[3'(1'-chloro-3-methyl-2'-oxopentan]-3,5-dichlor-4-methylbenzamide" to
--N-[3'-(1'-chloro-3'-methyl-2'-oxopentan]-3,5-dichloro-4-methylbenzamide--
```

Signed and Sealed this

Third Day of November, 1998

Attest:

Attesting Officer

BRUCE LEHMAN

Commissioner of Patents and Trademarks